US00PP14619P29

(12) United States Plant Patent
Vandenberg

(10) Patent No.: US PP14,619 P2
(45) Date of Patent: Mar. 23, 2004

(54) CHRYSANTHEMUM PLANT NAMED 'ARANGO'

(50) Latin Name: *Chrysanthemum×morifolium*
Varietal Denomination: Arango

(75) Inventor: Cornelis P. Vandenberg, Salinas, CA (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 10/452,067

(22) Filed: Jun. 2, 2003

(51) Int. Cl.[7] ..... A01H 5/00

(52) U.S. Cl. ..... Plt./295

(58) Field of Search ..... Plt./295

*Primary Examiner*—Anne Marie Grunberg
(74) *Attorney, Agent, or Firm*—C. A. Whealy

(57) ABSTRACT

A distinct cultivar of Chrysanthemum plant named 'Arango', characterized by its upright plant habit; freely flowering habit; daisy-type inflorescences that are about 6.5 cm in diameter; attractive bright yellow-colored ray florets and light green to bright yellow-colored disc florets; response time about 59 days; dark green-colored foliage; strong and thick peduncles; and excellent postproduction longevity with inflorescences and foliage maintaining good substance and color for about 21 days in an interior environment.

2 Drawing Sheets

Botanical classification/cultivar designation: *Chrysanthemum×morifolium* cultivar Arango.

BACKGROUND OF THE INVENTION

The present invention relates to a new and distinct cultivar of Chrysanthemum plant, botanically known as *Chrysanthemum×morifolium* and hereinafter referred to by the name 'Arango'.

The new Chrysanthemum is a product of a planned breeding program conducted by the Inventor in Salinas, Calif. and Alva, Fla. The objective of the breeding program is to create new cut Chrysanthemum cultivars having inflorescences with desirable colors and good form and substance.

The new Chrysanthemum originated from a cross-pollination made by the Inventor in January, 1998, in Salinas, Calif., of a proprietary *Chrysanthemum×morifolium* seedling selection identified as code number K550, not patented, as the female, or seed, parent with a proprietary *Chrysanthemum×morifolium* seedling selection identified as K642, not patented, as the male, or pollen, parent.

The cultivar Arango was discovered and selected by the Inventor as a flowering plant within the progeny of the stated cross-pollination in a controlled environment in Alva, Fla., in March, 1999. The selection of this plant was based on its desirable inflorescence color and good form and substance.

Asexual reproduction of the new Chrysanthemum by terminal cuttings taken in a controlled environment in Alva, Fla. since June, 1999, has shown that the unique features of this new Chrysanthemum are stable and reproduced true to type in successive generations.

SUMMARY OF THE INVENTION

Plants of the cultivar Arango have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Arango'. These characteristics in combination distinguish 'Arango' as a new and distnct cultivar:

1. Upright cut Chrysanthemum that is usually grown as a natural spray.
2. Freely flowering habit, about seven to eight inflorescences per flowering stem.
3. Daisy-type inflorescences that are about 6.5 cm in diameter.
4. Attractive bright yellow-colored ray florets and light green to bright yellow-colored disc florets.
5. Response time about 59 days.
6. Dark green foliage.
7. Strong and thick peduncles.
8. Excellent postproduction longevity with inflorescences and foliage maintaining good substance and color for about 21 days in an interior environment.

Plants of the new Chrysanthemum can be compared to plants of the female parent selection. In side-by-side comparisons conducted in Alva, Fla., plants of the new Chrysanthemum differed primarily from plants of the female parent selection in ray floret coloration as plants of the female parent selection had white-colored ray florets.

Plants of the new Chrysanthemum can be compared to plants of the male parent selection. In side-by-side comparisons conducted in Alva, Fla., plants of the new Chrysanthemum differed primarily from plants of the male parent selection in the following characteristics:

1. Plants of the new Chrysanthemum had smaller inflorescences than plants of the male parent selection.
2. Inflorescences of plants of the new Chrysanthemum produced a sparse amount of pollen whereas inflorescences of plants of the male parent selection produced a moderate amount of pollen.

Plants of the new Chrysanthemum can also be compared to plants of the *Chrysanthemum×morifolium* cultivar Yellow Vero, disclosed in U.S. Plant Pat. No. 8,058. In side-by-side comparisons conducted in Alva, Fla., plants of the new Chrysanthemum differed from plants of the cultivar Yellow Vero in the following characteristics:

1. Plants of the new Chrysanthemum had stronger stems than plants of the cultivar Yellow Vero.
2. Plants of the new Chrysanthemum flowered more uniformly than plants of the cultivar Yellow Vero.
3. Plants of the new Chrysanthemum had more ray florets per inflorescence than plants of the cultivar Yellow Vero.
4. Ray floret coloration of plants of the new Chrysanthemum was darker yellow than ray floret coloration of plants of the cultivar Yellow Vero.

BRIEF DESCRIPTION OF THE PHOTOGRAPHS

The accompanying colored photographs illustrate the overall appearance of the new Chrysanthemum, showing the colors as true as it is reasonably possible to obtain in colored reproductions of this type. Colors in the photographs may differ slightly from the color values cited in the detailed botanical description which accurately describe the colors of the new Chrysanthemum.

The photograph on the first sheet comprises a side perspective view of a typical flowering stem of 'Arango' grown as a natural spray.

The photograph on the second sheet comprises a close-up view of a typical flowering stem of 'Arango' grown as a natural spray.

DETAILED BOTANICAL DESCRIPTION

In the following description, color references are made to The Royal Horticultural Society Colour Chart, 1995 Edition, except where general terms of ordinary dictionary significance are used. The aforementioned photographs and following observations and measurements describe plants grown in La Ceja, Antioquia, Colombia, South America, under conditions which approximate commercial practice in a single-layer polyethylene-covered greenhouse. Two-week old rooted cuttings were planted on Aug. 19, 2002 and received 14 long day/short nights followed by short day/long nights until flowering. Plants were grown as single-stem natural spray cut Chrysanthemums. During the production time, the following environmental conditions were measured: day temperatures, 20 to 27° C.; night temperatures, 8 to 13° C.; and light levels, 4,000 to 6,000 foot-candles. Measurements and numerical values represent averages for six to ten typical flowering stems and were taken about ten weeks after the start of short days.

Botanical classification: *Chrysanthemum×morifolium* cultivar Arango.

Commercial classification: Daisy-type cut Chrysanthemum.

Parentage:

*Female or seed parent.*—Proprietary *Chrysanthemum×morifolium* seedling selection identified as code number K550, not patented.

*Male or pollen parent.*—Proprietary *Chrysanthemum×morifolium* seedling selection identified as code number K642, not patented.

Propagation:

*Type.*—Terminal tip cuttings.

*Time to rooting.*—About 10 to 14 days with soil temperatures of 18 to 21° C.

*Root description.*—Fine, fibrous and well-branched.

Plant description:

*Appearance.*—Herbaceous daisy-type cut flower that is typically grown as a natural spray.

*Flowering stem description.*—Aspect: Erect. Length: About 112 cm. Diameter (natural spray diameter): About 16 cm. Diameter (base of stem): About 6.5 mm. Internode length: About 3.25 cm. Texture: Pubescent; longitudinally ridged. Color: 146A.

*Foliage description.*—Arrangement: Alternate. Length: About 8.5 cm. Width: About 5.25 cm. Apex: Mucronate. Base: Attenuate to truncate. Margin: Palmately lobed; sinuses parallel to divergent. Texture: Upper and lower surfaces pubescent; smooth and leathery; veins prominent on lower surface. Color: Developing foliage, upper surface: Darker green than 147A. Developing foliage, lower surface: Darker green than 147B. Fully expanded foliage, upper surface: Close to 147A. Fully expanded foliage, lower surface: Close to 147B. Venation, upper surface: Close to 147A. Venation, lower surface: Close to 147B. Petiole: Length: About 1.5 cm. Diameter: About 4.5 mm. Color: Upper surface: 147A to 147B. Lower surface: Close to 146A.

Flowering description:

*Appearance.*—Daisy-type inflorescence form with elongated oblong-shaped ray florets. Inflorescences borne on terminals, arising from leaf axils. Disc and ray florets develop acropetally on a capitulum.

*Flowering response.*—Under natural conditions, plant flower in the autumn/winter in the Northern Hemisphere. At other times of the year, inflorescence initiation and development can be induced under short day/long night conditions (at least 13.5 hours of darkness). Plants exposed to two weeks of long day/short night conditions after planting followed by photoinductive short day/long night conditions flower about 59 days later when grown as a natural spray.

*Postproduction longevity.*—In an interior environment, inflorescences and foliage will maintain good color and substance for about 21 days in an interior environment.

*Quantity of inflorescences.*—Freely flowering habit, about seven to eight inflorescences per stem develop.

*Inflorescence size.*—Diameter: About 6.5 cm. Depth (height): About 2.75 cm. Diameter of disc: About 1.4 mm. Diameter of receptacle: About 7.5 mm.

*Inflorescence buds.*—Shape: Oblate. Height: About 6 mm. Diameter: About 7.5 mm. Color: More green than 147A.

*Ray florets.*—Shape: Elongated oblong; slightly concave to flat. Length: About 3.4 cm. Width: About 1 cm. Corolla tube length: About 3 mm. Apex: Emarginate. Base: Fused. Texture: Smooth, velvety, glabrous; longitudinally ridged. Aspect: Initially upright; when mature, mostly perpendicular to peduncle; with development, outwardly arching and curved downward. Number of ray florets per inflorescence: About 53 arranged in about three to four rows. Color: When opening and fully opened, upper surface: Brighter than 6A. When opening and fully opened, lower surface: 6A to 6B.

*Disc florets.*—Shape: Tubular, elongated. Length: About 5 mm. Width: Apex: About 1.5 mm. Base: About 1 mm. Number of disc florets per inflorescence: About 137. Color: Immature: Close to 144A.

Mature: Apex: 154A to 9A. Mid-section: Close to 150D. Base: Close to 155D.

*Phyllaries.*—Quantity per inflorescence: About 28. Length: About 9 mm. Width: About 3 mm. Shape: Lanceolate to deltoid. Apex: Acute. Base: Truncate. Margin: Entire. Texture, upper surface: Smooth, waxy. Texture, lower surface: Pubescent. Color, upper surface: 144A to 146A. Color, lower surface: More green than 147A.

*Peduncles.*—Length: First peduncle: About 22 cm. Fourth peduncle: About 25 cm. Seventh peduncle: About 33 cm. Diameter: About 3 mm. Angle: About 30° from vertical. Strength: Very strong. Texture: Pubescent. Color: 146A.

*Reproductive organs.*—Androecium: Present on disc florets only. Anther color: 9A. Amount of pollen: Sparse. Pollen color: 15A. Gynoecium: Present on both ray and disc florets.

*Seed/fruit.*—Seed and fruit production has not been observed.

Disease/pest resistance: Resistance to pathogens and pests common to Chrysanthemums has not been observed on plants grown under commercial conditions.

Temperature tolerance: Plants of the new Chrysanthemum have demonstrated good tolerance to low temperatures of 5° C. and high temperatures high temperatures of 35° C.

It is claimed:

1. A new and distinct cultivar of Chrysanthemum plant named 'Arango', as illustrated and described.

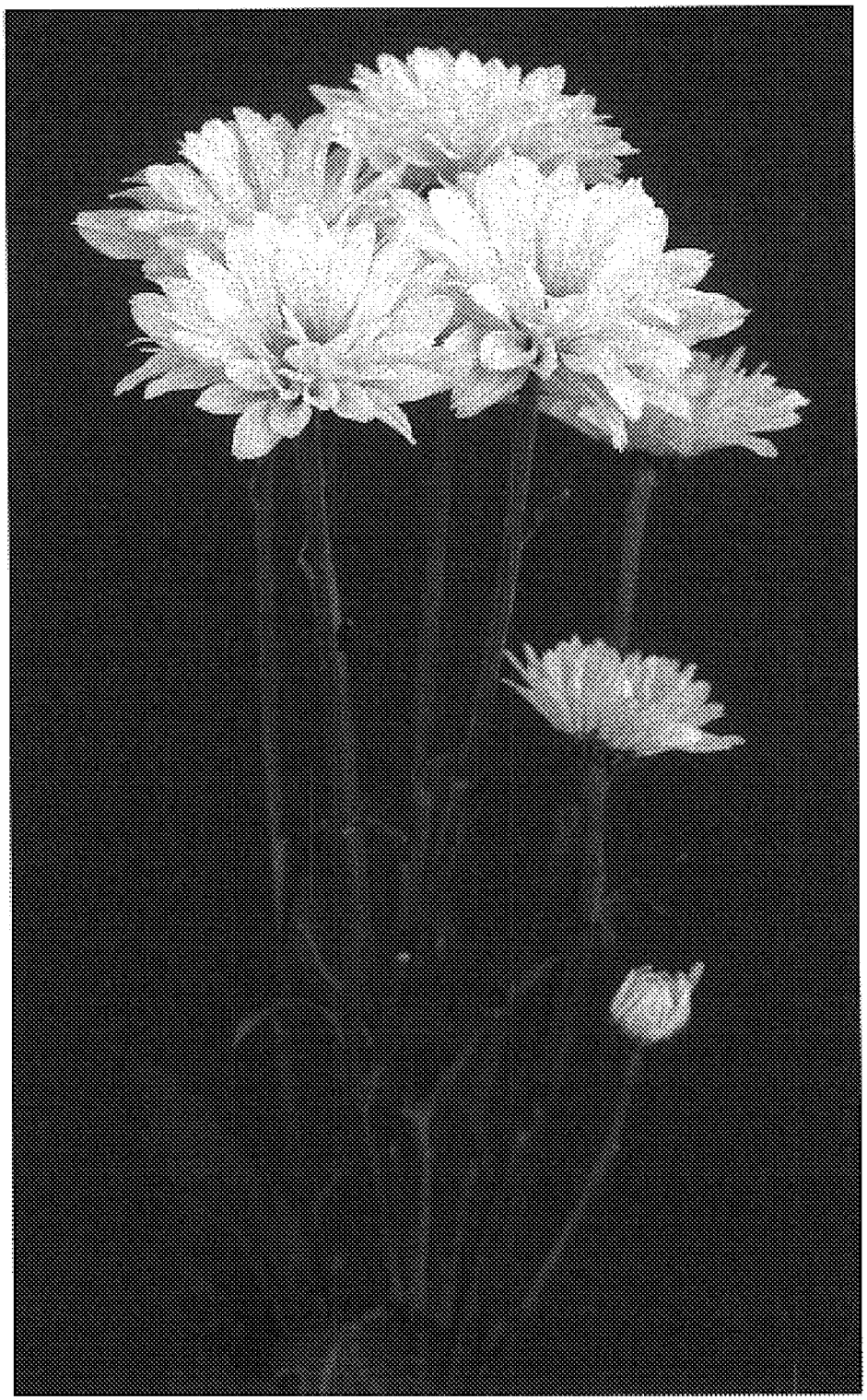

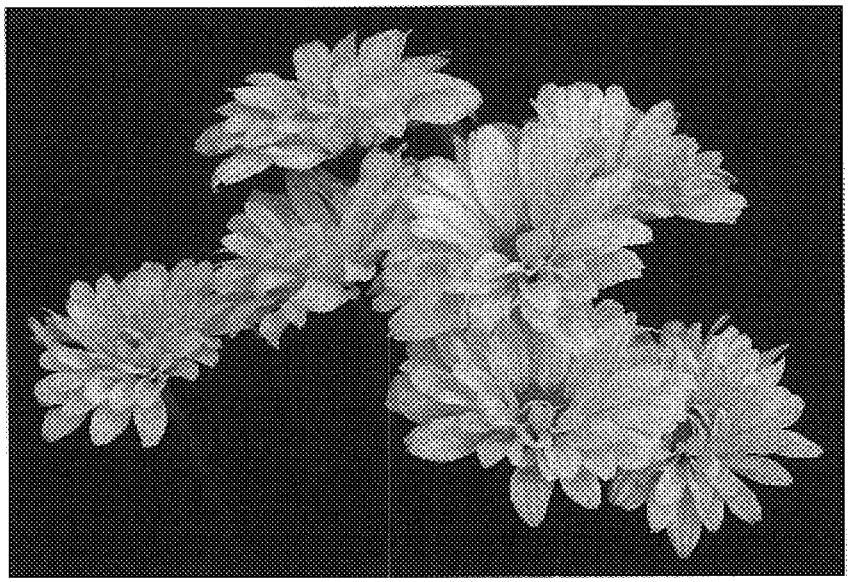

* * * * *